United States Patent [19]
Todo et al.

[11] Patent Number: 6,136,737
[45] Date of Patent: Oct. 24, 2000

[54] GLASS POWDER FOR DENTAL GLASS IONOMER CEMENT

[75] Inventors: Atsuhiro Todo; Michiko Hirasawa; Shinichi Kato, all of Tokyo, Japan

[73] Assignee: GC Corporation, Tokyo, Japan

[21] Appl. No.: 09/206,341

[22] Filed: Dec. 7, 1998

[30] Foreign Application Priority Data

Dec. 17, 1997 [JP] Japan ..................................... 9-363747

[51] Int. Cl.$^7$ .................................................. C03C 3/062
[52] U.S. Cl. .................................................. 501/73; 106/35
[58] Field of Search .............................. 501/57, 69, 70, 501/72, 73; 106/35

[56] References Cited

U.S. PATENT DOCUMENTS

| | | | |
|---|---|---|---|
| Re. 33,100 | 10/1989 | Ibsen et al. ................................ | 106/35 |
| 4,376,835 | 3/1983 | Schmitt et al. ............................ | 106/35 |
| 4,527,979 | 7/1985 | McLean et al. ........................... | 106/35 |
| 4,900,697 | 2/1990 | Akahane et al. .......................... | 501/57 |
| 5,063,257 | 11/1991 | Akahane et al. ......................... | 523/116 |
| 5,356,951 | 10/1994 | Yearn et al. .............................. | 523/116 |
| 5,641,347 | 6/1997 | Grabowski et al. ...................... | 106/35 |
| 5,962,550 | 10/1999 | Akahane et al. ......................... | 523/116 |

*Primary Examiner*—Karl Group
*Assistant Examiner*—David Sample
*Attorney, Agent, or Firm*—Oblon, Spivak, McClelland, Maier & Neustadt, P.C.

[57] ABSTRACT

A glass powder for dental glass ionomer cement is disclosed, comprising a fluoroaluminosilicate glass powder for dental glass ionomer cement having a specific gravity of 2.4~4.0, a mean particle size of 0.02~4 μm, and a BET specific surface area of 2.5~6.0 m$^2$/g. Further, it preferably has a maximum particle size of less than 4 μm and contains 10~21% by weight of $Al^{3+}$, 9~21% by weight of $Si^{4+}$, 1~20% by weight of $F^-$, and 10~34% by weight in total of $Sr^{2+}$ and/or $Ca^{2+}$ in its components. The glass powder for dental glass ionomer cement of the invention can impart superior surface smoothness and film thickness, while utilizing superior characteristics inherent to the conventional dental glass ionomer cement, such as superior biocompatibility and adhesive strength.

6 Claims, No Drawings

GLASS POWDER FOR DENTAL GLASS IONOMER CEMENT

FIELD OF THE INVENTION

The present invention relates to a glass powder for dental glass ionomer cement. More particularly, the present invention relates to a fluoroaluminosilicate glass which is provided for a dental glass ionomer cement.

BACKGROUND OF THE INVENTION

A dental glass ionomer cement is a dental cement having many characteristics such that it has superior biocompatibility and adhesive strength and excellent esthetics and that it can be expected to have a caries preventing effect by fluorine contained in the glass powder. By utilizing many of these characteristics, the dental glass ionomer cement is used for wide applications in the dental field, such as filling of a caries cavity, cementing of a crown, an inlay, a bridge, or an orthodontic bracket or band, lining of a cavity, core build up, pit and fissure sealing, and adhering at the time of filling a dental composite resin.

However, the dental glass ionomer cement involves such a defect that if it comes into contact with a water such as saliva at the initial stage of setting, the setting reaction is inhibited, whereby the final physical properties are decreased. This is caused by the fact that since a acid-base reaction between a polycarboxylic acid (acid) and a fluoroaluminosilicate glass (base) in the dental glass ionomer cement is carried out in the presence of water, the dental glass ionomer cement is liable to be influenced by the water. And, there is generated a phenomenon in which a surface which has come into contact with the water at the initial stage of setting becomes brittle, and the cement becomes chalky, whereby the esthetics are spoiled. With respect to this issue, there have, hitherto been tried many improvements. There are laid open technologies for making the setting time, such as, for example, addition of a chelating agent in Japanese Patent Publication No. 54-21858; addition of a fluorocomplex salt in Japanese Patent Laid-Open No. 57-2210; and addition of a polymerizable unsaturated organic compound and a polymerization catalyst to the liquid component in Japanese Patent Laid-Open No. 6-27047. In addition, the present inventor has proposed a technology utilizing a redox reaction by addition of an oxidation-reduction catalyst in which the setting reaction takes place even without irradiation with a visible light in Japanese Patent Laid-Open No. 8-26925. By using these proposed dental glass ionomer cement, the problems which occur due to the contact with a water at the initial stage of setting, such as brittleness and disintegration, can be overcome, the manipulability is greatly improved by the photocuring, and the physical properties such as adhesive strength to a tooth, bending strength, and transparency are improved.

On the other hand, as a defect of the dental glass ionomer cement, it is pointed out that in case of using it for filling, the polished surface after setting is rough, and the film thickness is thick.

In other words, due to the fact that the smoothness of the polished surface of a restoration is insufficient, there is an inconvenience that in the oral cavity, it is rough and unpleasant, whereby a patient is liable to complain of a feeling of physical disorder. In case of using it for filling of anterior teeth in particular, there is generated a phenomenon that the esthetics are somewhat inferior, and since the film thickness is thick, in case of using it for cementing of a crown or an inlay, the prosthesis is liable to come up and a fittness becomes worse. Actually, when the dental glass ionomer was compared with the dental composite resin and dental resin cement, with respect to the ten-point average surface roughness immediately after the setting, the dental composite resin showed about 3.0 $\mu$m, whereas the dental glass ionomer cement showed a large value as about 8.0 $\mu$m; and with respect to the film thickness, the dental resin cement exhibited about 5~10 $\mu$m, whereas the dental glass ionomer cement exhibited a large value as about 15~20 $\mu$m.

As described above, the improvements in the dental glass ionomer cement have hitherto been focused only on the improvements in the physical properties or manipulability.

SUMMARY OF THE INVENTION

Thus, an object of the present invention is to develop a dental glass ionomer cement which while utilizing superior characteristics inherent to the conventional dental glass ionomer cement, such as superior biocompatibility and adhesive strength, can overcome the defects of the conventional dental glass ionomer cement by imparting superior surface smoothness and film thickness and which can be used with confidence for the dental treatment such as filling or cementing.

The present inventor has made extensive and intensive investigations in order to achieve the above-described objects. As a result, it has been found that by using a fluoroaluminosilicate glass powder to be used in a dental glass ionomer cement, whose particle size has been adjusted finer by pulverization, the activity of a glass is not lowered, while the superior characteristics inherent to the conventional dental glass ionomer cement, such as superior biocompatibility and adhesive strength can be kept as they are and that in case of using it as a filler, it is possible to undergo filling with superior surface smoothness and without a feeling of physical disorder, whereas in case of using it as a cementing material, the film thickness can be made thin, whereby the cementing without causing a prosthesis to come up can be realized, leading to accomplish the present invention.

That is, the glass powder for dental glass ionomer cement according to the present invention comprises a fluoroaluminosilicate glass powder for dental glass ionomer cement having a specific gravity of 2.4~4.0, a mean particle size of 0.02~4 $\mu$m, and a BET specific surface area of 2.5~6.0 $m^2/g$.

DETAILED DESCRIPTION OF THE INVENTION

As the fluoroaluminosilicate glass powder for dental glass ionomer cement according to the present invention, a known fluoroaluminosilicate glass powder which has hitherto been used as a powder component of a dental glass ionomer cement can be used after being pulverized. However, since it is preferred that the fluoroaluminosilicate glass powder to be used is one in which the glass activity is not lowered even after being pulverized more finely, a fluoroaluminosilicate glass powder containing 10~21% by weight of $Al^{3+}$, 9~21% by weight of $Si^{4+}$, 1~20% by weight of $F^-$, and from 10~34% by weight in total of $Sr^{2+}$ and/or $Ca^{2+}$ in its components is suitable.

The fluoroaluminosilicate glass powder according to the present invention can be prepared by the conventional glass-making technique. For example, glass raw materials selected from silica, alumina, aluminum hydroxide, aluminum silicate, mullite, calcium silicate, strontium silicate, sodium silicate, aluminum carbonate, calcium carbonate, strontium carbonate, sodium carbonate, sodium fluoride, calcium fluoride, aluminum fluoride, strontium fluoride, aluminum phosphate, calcium phosphate, strontium phosphate, sodium phosphate, etc. are weighed, molten at high temperatures of at least 1,000° C., cooled, and then pulverized to prepare a fine powder.

The fluoroaluminosilicate glass powder as the glass powder for dental glass ionomer cement according to the present invention must have a mean particle size in the range of 0.02~4 µm. If the mean particle size exceeds 4 µm, the surface smoothness is lowered and the setting reaction is slow and hence, these are not proper. On the other hand, in case that a fine powder having a mean particle size of less than 0.02 µm is used, an absolute amount of the powder is hardly incorporated into the liquid, and the physical properties are liable to be decreased. Hence, such is not proper neither. The particle size can be measured by conventional means. Taking into consideration possible influences of the maximum particle size to the surface smoothness and film thickness, it is preferred that the maximum particle size be controlled to be less than 4 µm.

Also, the glass powder according to the present invention must have a specific gravity in the range of 2.4~4.0. The specific gravity can be measured by a conventional method by using a specific gravity bottle, etc. In case that the specific gravity falls outside the above-defined range, the reactivity of the glass is lowered, leading a reduction in the physical properties and hence, such is not proper.

In addition, the glass powder according to the present invention must have a BET specific surface area in the range of from 2.5~6.0m$^2$/g. In case that the BET specific surface area which is a factor to greatly influence the reaction with the liquid component is less than 2.5m$^2$/g, the setting reaction is slow, whereas in case that it exceeds 6.0 m$^2$/g, the setting reaction is too fast and, such is not proper.

As a matter of course, the glass powder according to the present invention can be subjected to surface processing with a fluoride or a polymerizable ethylenically unsaturated double bond-containing organic compound or an acid, and the surface processing can be carried out by conventional methods. Also, as a matter of course, as the liquid component which is used in combination with the glass powder for dental glass ionomer cement according to the present invention, conventional liquids for dental glass ionomer cement, containing a polymer acid such as a polyacrylic acid or an acrylic acid copolymer, can be used.

The present invention is hereunder described in more detail with reference to the following Examples, but it is not be construed that the invention is limited thereto.

EXAMPLE 1

23 g of aluminum oxide, 41 g of silicic anhydride, 10 g of strontium fluoride, 13 g of aluminum phosphate, and 13 g of calcium fluoride were thoroughly mixed with each other, and the mixture was kept in a high-temperature electric furnace at 1,200° C. for 5 hours, thereby melting the glass. After the melting, the molten glass was cooled and pulverized for 10 hours with a ball mill. Thereafter, the pulverized glass was further added with distilled water as a pulverization assistant agent and pulverized for 20 hours with a vibration mill, and a powder which passed through a 200-mesh sieve (according to ASTM) was defined to be a glass powder. With 100g of this glass powder was mixed 100 g of a 1% titanium-sodium fluoride aqueous solution to prepare a slurry. The water was evaporated off with a dryer at 120° C. to achieve the surface processing, thereby preparing a glass powder for dental glass ionomer cement. The thus obtained glass powder had a specific gravity of 3.3, a mean particle size of 2.3 µm, a maximum particle size of 3.9 µm, and a BET specific surface area of 4.3 m$^2$/g.

With 3.0 g of this glass powder was mixed 1.0 g of a commercially available dental glass ionomer cement liquid (made by GC Corporation, a trade name: "CC Fuji Ionomer Type II"® liquid), and the mixture was measured for various physical properties by the following test methods. As a result, the working time was 3 minutes and 15 seconds, the compressive strength was 200 MPa, the film thickness was 8.5 µm, and the ten-point average roughness after the polishing was 1.5 µm.

The compressive strength was measured based on the test method as described in JIS T6602 for a dental zinc phosphate cement. Also, the film thickness was measured according to the test method of JIS T6602. The working time was evaluated by touching a cement mixture by a tip of a spatula for mixing a cement and measuring a time until the fluidity of the cement mixture had been lost. In addition, the ten-point average roughness was measured in the following manner. That is, a cement mixture was filled in a glass-made ring having an inner diameter of 10 mm and a height of 2 mm for allowing it to set, kept in a chamber at 37° C. having a relative humidity of 100% for 24 hours, then polished by a polishing material (a trade name "Super Snap Red 12a"®; made by Shofu Co., Ltd.), and then measuring the ten-point average roughness with a surface roughness meter (a trade name "Surfcorder SE-40H"®; manufactured by Kosaka Laboratory, Ltd.).

EXAMPLE 2

23 g of aluminum oxide, 41 g of silicic anhydride, 10 g of strontium fluoride, 13 g of aluminum phosphate, and 13 g of calcium fluoride were thoroughly mixed with each other, and the mixture was kept in a high-temperature electric furnace at 1,200° C. for 5 hours, thereby melting the glass. After the melting, the molten glass was cooled and pulverized for 10 hours with a ball mill. Thereafter, the pulverized glass was further added with distilled water as a pulverization assistant agent and pulverized for 20 hours with a vibration mill, and a powder which had passed through a 200-mesh sieve (according to ASTM) was defined to be a glass powder. To 100 g of this glass powder was added 20 g of a 5% ethanol solution of γ-methacryloxypropyl trimethoxysilane and thoroughly mixed in a mortar. Thereafter, the resulting mixture was dried at 120° C. for 2 hours with a steam dryer to achieve the silane processing. To 100 g of the thus silane-processed powder was added 0.25 g of p-toluenesulfonyl hydrazide and thoroughly mixed to prepare a glass powder for dental glass ionomer cement. The thus obtained glass powder had a specific gravity of 3.3, a mean particle size of 2.2 µm, a maximum particle size of 3.9 µm, and a BET specific surface area of 4.0 m$^2$/g.

With 3.0 g of this glass powder was mixed 1.0 g of a commercially available dental glass ionomer cement liquid (made by GC Corporation, a trade name: "GC Fuji Ionomer Type IILC"®; liquid), and the mixture was measured for various physical properties. The setting was carried out upon irradiation with a light for 20 seconds by using a commercially available light irradiation apparatus (made by GC Corporation, a trade name "GC New Light VL-II"®). As a result, the working time was 3 minutes and 30 seconds, the compressive strength was 230 MPa, the film thickness was 7.2 µm, and the ten-point average roughness after the polishing was 1.5 µm.

EXAMPLE 3

23 g of aluminum oxide, 30 g of silicic anhydride, 30 g of strontium fluoride, 5 g of aluminum phosphate, and 12 g of aluminum fluoride were thoroughly mixed with each other, and the mixture was kept in a high-temperature electric furnace at 1,300° C. for 5 hours, thereby melting the glass. After the melting, the molten glass was cooled and pulverized for 10 hours with a ball mill. Thereafter, the pulverized glass was further added with distilled water as a pulverization assistant agent and pulverized for 20 hours with a vibration mill, and a powder which had passed through a 200-mesh sieve (according to ASTM) was defined to be a glass powder. With 100 g of this glass powder was mixed 100 g of a 1% titanium-sodium fluoride aqueous solution to prepare a slurry. The water was evaporated off with a dryer at 120° C. to achieve the surface processing, thereby preparing a glass powder for dental glass ionomer cement. The thus obtained glass powder had a specific gravity of 3.0, a mean particle size of 2.0 $\mu$m, a maximum particle size of 3.6 $\mu$m, and a BET specific surface area of 4.4 m$^2$/g.

With 1.8 g of this glass powder was intimately mixed 1.0 g of a commercially available dental glass ionomer cement liquid (made by GC Corporation, a trade name: a "GC Fuji I"® liquid), and the mixture was measured for various physical properties. As a result, the working time was 2 minutes and 00 second, the compressive strength was 200 MPa, the film thickness was 8.0 $\mu$m, and the ten-point average roughness after the polishing was 2.2 $\mu$m.

EXAMPLE 4

23 g of aluminum oxide, 30 g of silicic anhydride, 30 g of strontium fluoride, 5 g of aluminum phosphate, and 12 g of aluminum fluoride were thoroughly mixed with each other, and the mixture was kept in a high-temperature electric furnace at 1,300° C. for 5 hours, thereby melting the glass. After the melting, the molten glass was cooled and pulverized for 10 hours with a ball mill. Thereafter, the pulverized glass was further added with distilled water as a pulverization assistant agent and pulverized for 20 hours with a vibration mill, and a powder which had passed through a 200-mesh sieve (according to ASTM) was defined to be a glass powder. To 100 g of this glass powder was added 20 g of a 5% ethanol solution of y-methacryloxypropyl trimethoxysilane and thoroughly mixed in a mortar. Thereafter, the resulting mixture was dried at 120° C. for 2 hours with a steam dryer to achieve the silane processing. To 100 g of the thus silaneprocessed powder was added 0.25 g of p-toluenesulfonyl hydrazide and thoroughly mixed to prepare a glass powder for dental glass ionomer cement. The thus obtained glass powder had a specific gravity of 3.0, a mean particle size of 2.2 $\mu$m, a maximum particle size of 3.5 $\mu$m, and a BET specific surface area of 4.3 m$^2$/g.

With 2.0 g of this glass powder was intimately mixed 1.0 g of a commercially available dental glass ionomer cement liquid (made by GC Corporation, a trade name: "GC Fuji PLUS"® liquid), and the mixture was measured for various physical properties. As a result, the working time was 2 minutes and 30 seconds, the compressive strength was 220 MPa, the film thickness was 8.0 $\mu$m, and the ten-point average roughness after the polishing was 2.7 $\mu$m.

COMPARATIVE EXAMPLE 1

As a conventional dental glass ionomer cement, a trade name "GC Fuji I" (made by GC Corporation) and its liquid and powder were mixed with each other pursuant to the indications according to the instruction manual, and the mixture was measured for various physical properties. As a result, the working time was 2 minutes and 00 second, the compressive strength was 20 OMPa, the film thickness was 15.0 $\mu$m, and the ten-point average roughness after the polishing was 6.2 $\mu$m.

COMPARATIVE EXAMPLE 2

As a conventional dental glass ionomer cement, a trade name "GC Fuji Ionomer Type II LC"® (made by GC Corporation) and its liquid and powder were mixed with each other pursuant to the indications according to the instruction manual, and the mixture was measured for various physical properties. As a result, the working time was 3 minutes and 15 seconds, the compressive strength was 200 MPa, the film thickness was 20 $\mu$m, and the ten-point average roughness after the polishing was 5.3 $\mu$m.

As described above in detail, as compared with a case where a dental glass ionomer cement is prepared by using a conventional glass powder for dental glass ionomer cement, in case of preparing a dental glass ionomer cement by using the glass powder for dental glass ionomer cement according to the present invention, not only the ten-point average roughness is particularly small so that in case using it for filling, the surface smoothness is superior, but also the film thickness is thin so that in case of using it for cementing, it is possible to undergo cementing with good fittness without causing a prosthesis to come up. Accordingly, the present invention greatly contributes to the dental field.

While the invention has been described in detail and with reference to specific embodiments thereof, it will be apparent to one skilled in the art that various changes and modifications can be made therein without departing from the spirit and scope thereof.

What is claimed is:

1. A glass powder for dental glass ionomer cement, comprising a fluoroaluminosilicate glass powder for dental glass ionomer cement having a specific gravity of 2.4 to about 4.0, a mean particle size of 0.02 to about 4 $\mu$m, a BET specific surface area of 2.5 to about 6.0 m$^2$/g, and a maximum particle size of less than 4 $\mu$m.

2. The glass powder for dental glass ionomer cement as claimed in claim 1, wherein said fluoroaluminosilicate glass powder is a fluoroaluminosilicate glass powder containing 10~21% by weight of Al$^{3+}$, 9~21% by weight of Si$^{4+}$, 1~20% by weight of F$^-$, and 10 to 34% by weight in total of Sr$^{2+}$ or Ca$^{2+}$ or both in its components.

3. The glass powder for dental glass ionomer cement as claimed in claim 1, having a specific gravity of 3.0–3.3.

4. The glass powder for dental glass ionomer cement as claimed in claim 1, having a mean particle size of 2.0–2.3 $\mu$m.

5. The glass powder for dental glass ionomer cement as claimed in claim 1, having a maximum particle size of from 3.5–3.9 $\mu$m.

6. The glass powder for dental glass ionomer cement as claimed in claim 1, having a BET specific surface area of 4.0–4.4 m$^2$/g.

* * * * *